United States Patent [19]

Pagano et al.

[11] Patent Number: 5,777,891
[45] Date of Patent: Jul. 7, 1998

[54] METHOD FOR REAL-TIME ULTRASONIC TESTING SYSTEM

[75] Inventors: Dominick Pagano, Weston; Brian Mackay, Bethel; James Norris, Georgetown, all of Conn.

[73] Assignee: Dapco Industries Inc., Ridgefield, Conn.

[21] Appl. No.: 703,616

[22] Filed: Aug. 23, 1996

Related U.S. Application Data

[63] Continuation of Ser. No. 393,943, Feb. 22, 1995, abandoned, which is a continuation of Ser. No. 257,933, Jun. 9, 1994, abandoned, which is a continuation of Ser. No. 124,837, Sep. 21, 1993, abandoned, which is a continuation of Ser. No. 696,505, May 7, 1991, abandoned.

[51] Int. Cl.$^6$ .......................... G01N 29/06; G01N 29/18
[52] U.S. Cl. ...................... 364/507; 73/636; 73/639; 73/598
[58] Field of Search .................... 364/552, 550, 364/551.01, 507, 508, 217; 73/635, 636, 639, 641, 598, 602

[56] References Cited

U.S. PATENT DOCUMENTS

| 4,174,636 | 11/1979 | Pagano | 73/636 |
|---|---|---|---|
| 4,213,183 | 7/1980 | Barron et al. | 364/552 |
| 4,222,275 | 9/1980 | Scholl et al. | 73/636 |
| 4,487,071 | 12/1984 | Pagano et al. | 73/636 |
| 4,593,569 | 6/1986 | Joy | 73/639 |
| 4,785,668 | 11/1988 | Pagano | 73/622 |
| 4,872,130 | 10/1989 | Pagano | 364/507 |
| 4,947,351 | 8/1990 | Moran et al. | 364/550 |
| 5,030,911 | 7/1991 | Lam | 364/507 |
| 5,063,780 | 11/1991 | Landry et al. | 73/622 |

OTHER PUBLICATIONS

Hwang, Shiming; Masters Thesis; Univ. of Conn.; 1987; "Representations and Processing of 3–Dimensional, Ultrasonic–Based, Information For Real Time Pattern Recognition".

Gandhi, Rajeev; Masters Thesis; Univ. of Conn.; 1984 "Real Time Pattern Recognition".

Bansal, Veena; Masters Thesis; Univ. of Conn.; 1987; "A Syntactic Approach for Pattern Recognition in Ultrasonic––Based, Nondestructive Test Applications".

Rogovsky et al; Ultrasonic Flaw Evaluation in Rails with Assistance of Programmable Calculator; ASNT National Fall Conference, Oct. 1980, Houston, TX (73/636).

*Primary Examiner*—Michael Zanelli
*Attorney, Agent, or Firm*—Lieberman & Nowak, LLP

[57] ABSTRACT

An ultrasonic real-time inspection method which is user-friendly in an interactive environment to provide ease of operation, as well as a combination of consistency, thoroughness, and speed of operation in flaw detection not achievable by other methods. The method offers significantly increased pattern recognition capability, which provides greater automation potential and reduced missed detection and false alarm rates.

8 Claims, 20 Drawing Sheets

\*\*\* DAPCO RTS-1000 RAIL TESTING SYSTEM \*\*\*    10:21 TUE

PATTERN RECOGNITION MENU

| LEFT RAIL | | | RIGHT RAIL | | |
|---|---|---|---|---|---|
| START FEET INCH | LENGTH INCHES | PATTERN | START FEET INCH | LENGTH INCHES | PATTERN |
| 2  10.4 | 0.938 | SWO | 0  8.69 | 1.62 | VSH |
| 2  10.4 | 0.938 | SWO | 1  0.625 | 0.938 | VSH |
| 2  11.5 | 0.188 | SWO | 1  2.06 | 0.938 | VSH |
| 3  1.56 | 1.12 | SWO | 1  4.5 | 0.938 | VSH |
| 3  3.19 | 1.19 | SWO | 1  8.62 | 5.25 | SWO |
| 3  3.69 | 0.5 | SWO | 1  8.62 | 5.25 | SWO |
| 3  5.25 | 0.75 | SWO | 1  10.9 | 2.44 | VSH |
| 3  11.8 | 0.25 | SWO | 1  11.4 | 1 | SWO |
| 3  11.9 | 0.688 | SWO | 2  0.812 | 1.19 | SWO |
| 4  1.56 | 1.19 | VSH | 2  0.938 | 0.938 | SWO |
| 4  1.69 | 0.0625 | SWO | 2  2.69 | 1.94 | HWO |
| 4  2.81 | 0.188 | EOT | 2  3.5 | 1.12 | SWO |
|  |  |  | 2  4.12 | 0.812 | SWO |
|  |  |  | 2  5.62 | 0.688 | SWO |
|  |  |  | 2  7.75 | 0.0625 | SWO |
|  |  |  | 2  7.81 | 1.19 | SWO |
|  |  |  | 2  8.19 | 1.31 | HWO |
|  |  |  | 2  9.5 | 1.12 | SWO |
|  |  |  | 2  10.4 | 0.938 | SWO |
|  |  |  | 2  10.6 | 0.938 | SWO |

BSCAN MENU

F1 LEFT UP

F2 LEFT DOWN

F3 RIGHT UP

F4 RIGHT DOWN

F10 QUIT

FIG. 19

METHOD FOR REAL-TIME ULTRASONIC TESTING SYSTEM

This application is a continuation of application Ser. No. 08/393,943 filed Feb. 22, 1995, now abandoned, which in turn is a continuation application Ser. No. 08/257,933 filed Jun. 9, 1994, now abandoned, which in turn is a continuation of application Ser. No. 08/124,837, filed Sep. 21, 1993, now abandoned, which in turn is a continuation of application Ser. No. 07/696,505, filed May 7, 1991, now abandoned.

FIELD OF THE INVENTION

This invention relates to real-time ultrasonic testing systems and, more-particularly, to such a system which is user-friendly and provides extremely comprehensive display features.

BACKGROUND OF THE INVENTION

With the current technology in ultrasonic testing, especially in the areas of rail testing, a heavy burden is placed on the equipment operator to decide if a set of responses indicates a flaw (such as a cracked rail), or a normal condition (such as a rail junction). Typically, the operator must verify any decisions he makes by stopping the test equipment and manually inspecting the area in question. This process of manual reinspection leads to tremendous inefficiency and lost time. This process can be done automatically and in real-time by the instant invention.

The objective of the invention is to assist the operator by making test decisions automatically at high speed. The operator no longer needs to interpret and verify each response from the test equipment. The system also represents a quantum leap in visualizing the flaws present in a test piece, and can produce a color 2-D graph of the test piece showing the orientation, shape and size of each flaw detected. The operator has the option of inspecting each of the test decisions, and the graphical information, before accepting a decision made by the system.

SUMMARY OF THE INVENTION

The instant invention provides amuser-friendly, interactive environment to provide ease of operation, as well as a combination of consistency, thoroughness, and speed of operation in flaw detection not achievable by other methods. The system significantly-increases pattern recognition capability, which promises a greater automation potential, and reduced missed detection and false alarm rates. Also, the system provides an increased user-visualization capability during operation, through a careful 3-dimensional analysis of collected data sets and graphic presentation. The invention will also maintain testing speeds of 15–25 miles per hour, depending upon test density and vehicular selection.

In order to provide a high level of capability, while maintaining a high data testing rate, a distributed, multiple processor configuration is used for the high speed portion of the system. The user interface consists of a state of the art PC for user control, data storage, and report generation. In addition, a special graphics-devoted computer (PC with a high performance graphics interface and monitor) is provided for on-line visualization capability. Overall, the instant invention represents a true next-generation solution in the area of real-time non-destructive testing of rails and other test pieces.

BRIEF DESCRIPTION OF THE DRAWINGS

FIGS. 16A–20 show typical display generated for use with the invention.

DETAILED DESCRIPTION OF THE INVENTION

The Rail Inspection System of the instant invention is composed of the following major sections:

Vehicle, Hi-Rail Automotive Van.

Wheel Probe Carriage (Attached to the Hi-Rail Vehicle).

Ultrasonic Wheel Probes; two for each rail; mounted on the carriage.

Liquid Couplant System included in the Vehicle and Carriage.

Ultrasonic-Based, Computerized, Flaw Detection/ Recognition System.

The Hi-Rail Vehicle houses and provides support and power for the entire Hi-Rail Rail Inspection System.

The Wheel Probe Carriage is carried either under the rear deck of the vehicle, or folded up into the rear compartment, and provides an adjustable surface for mounting of the wheel probes which carry the ultrasonic transducers.

Two Wheel Probes are provided for each rail. Each wheel probe consists of a set of ultrasonic transducers mounted axially and contained within a fluid-filled wheel, which rolls on the rail surface.

Two Wheel Probes are provided for each rail. Each wheel probe consists of a set of ultrasonic transducers mounted axially and contained within a fluid-filled wheel which rolls on the rail surface.

The Liquid Couplant System provides the liquid (water) for assuring that the transducer-generated ultrasonic waves are efficiently coupled to the rails by the wheel probes. The couplant system will pump a total of up to twenty gallons of couplant per hour in front of the wheel probes.

The Ultrasonic-Based, Computerized, Flaw Detection/ Recognition System has been designed to apply computer processing methods in real-time to ultrasonic-based information about rail integrity. The system is self-contained, user-friendly, and offers a high-speed, consistent, decision-making environment for rail testing applications.

Figure 1:
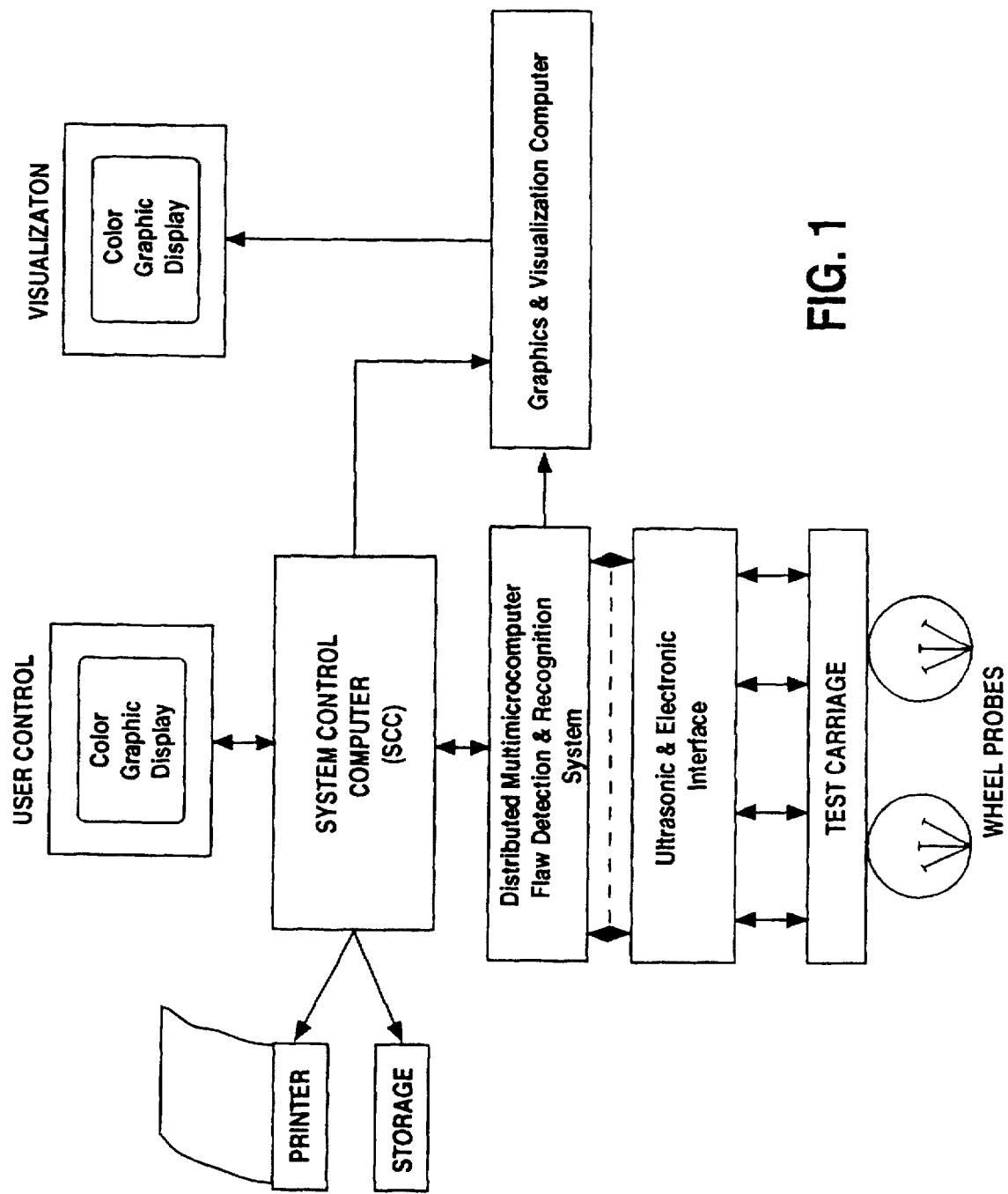
FIG. 1 is a block diagram of the rail inspection system of the instant invention.

The major components in the system are shown in FIG. 1. Four ultrasonic wheel probes containing the ultrasonic transducers, and two paint-gun solenoids are located externally on the test carriage. The Ultrasonic & Electronic Interface, and the Distributed Multimicrocomputer Flaw Detection & Recognition System, are mounted in nineteen inch racks, which are located in the overhead at the rear of the Hi-Rail vehicle. Two state of the art PC computers provide the user interface to the system. The system control computer supports user-system interaction, data archiving, and report generation. The second computer is configured as a high speed graphics support system, to allow the system to provide enhanced graphics/visualization of the test data.

Stored, precalibrated data sets allow immediate set-up of the system for alternative rail sizes. Hard-copy exception reports may be generated during the testing process upon demand. The system provides the operator with a near real-time presentation of the rail flaw content and identity for both rails simultaneously during operation on a color graphics display. A second display unit contains a touch-sensitive screen through which the operator can control the operation of the test system. Virtually all of the control functions are accomplished via menu selection by pressing predefined areas of the touch sensor, or alternatively through predefined function keys on an alphanumeric keyboard.

Normal operation, once the system has been calibrated, is semi-automatic. An operator is required to start-up the system and load a set of test parameters before the system will begin collecting data. The operator may also specify data such as the location of the rail which is to be tested for inclusion on the hard-copy report. As the test vehicle moves along the rail, the ultrasonic data which is being collected is processed by the distributed computing system to recognize the specific ultrasonic data profiles peculiar to each flaw type of interest. This processing includes the detection of potential flaw "events", creation of a volume profile of the response locations; and comparative evaluation of the resulting multi-channel 3-dimensional data with built-in flaw models to complete the detection/recognition process. As probable defect areas are recognized by the system, the rail is automatically marked by paint guns to help locate areas for repair. The operator may review the graphical presentation of the recognized data set to confirm the analysis, or the marked rail areas, may be scanned for verification. After confirmation, the system will continue with its data logging and reporting functions. All system control functions are provided through "Test Parameter Update" screens on the control computer. All test parameters can be stored and recalled at any time for quick and efficient setups for varying rail sizes, thus ensuring repeatable testing for each rail size.

Figures 2A, 2B:
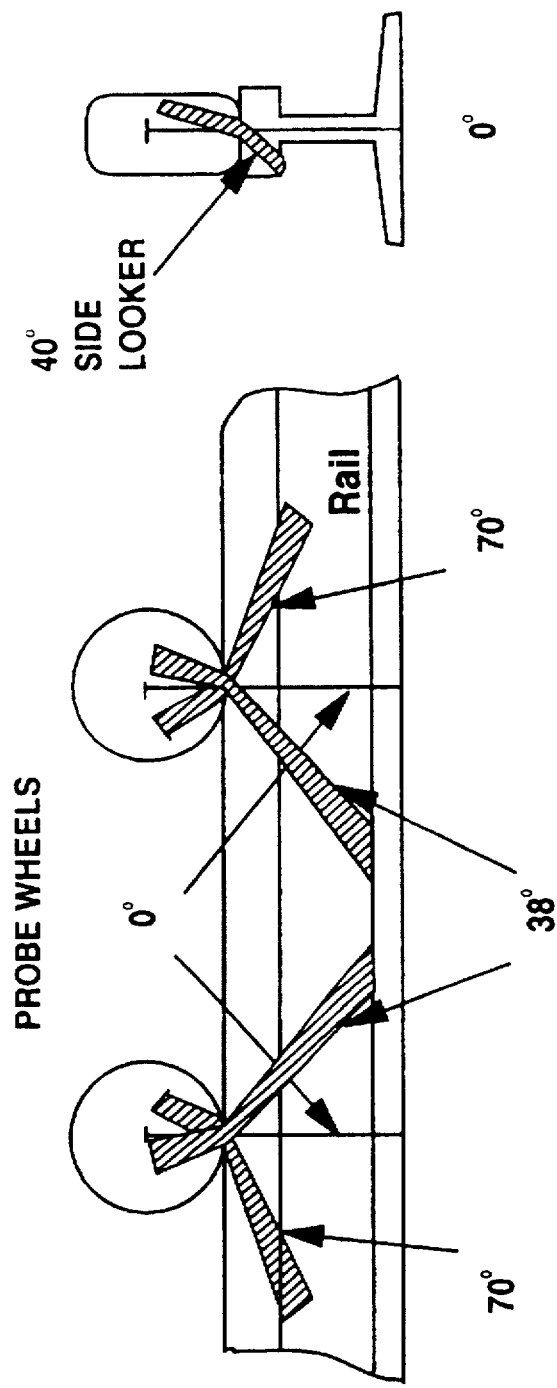
FIGS. 2A and 2B illustrate transducer orientation.

The transducer orientation is given in FIG. 2, where the approximate ultrasonic regions covered by each transducer are shown in relation to the rail orientation. A single sensitivity (threshold) is provided for each ultrasonic channel, and is controllable by the operator in terms of percent of full scale of the amplifier output. Further, the software processing for the collected data provides an additional and subsequent capability to increase the threshold dynamically within the test time. The system monitors the data from the pulsed transducers at a maximum resolution of 1/16 inch of vehicle movement. As the vehicle speed increases, the test density (pulses per inch) decreases to insure time to recover the ultrasonic data; however, the position resolution of the data is maintained at 1/16 inch. The system configuration provides for a total of twenty data channels, four of which monitor the "bottom of rail" signal and are used as probe wheel channels, and sixteen of which are used as flaw detection channels. Rail marking is accomplished by a single paint gun for each rail. Both paint guns are located externally on the carriage assembly to the rear of the test probes.

The semi-automatic calibration of the system is achieved by having the previously set values for amplifier gains, threshold settings, gates, etc., saved and restored in a file on the main computer's disk. The initial values for each rail size are determined by the system operator. These initial calibrations are accomplished by having the operator change the existing values via the touch-sensor or keyboard, while monitoring the incoming data and test results on an oscilloscope and the graphic display, respectively. Adjustments to controls on the printed circuit boards are only necessary during periodic maintenance checks, and should only be attempted by qualified personnel.

A hard-copy daily test report is maintained in a text file stored on the main computer's hard disk. This report is used to maintain a chronological log of the vehicle's movement during the work day. The total time tested, delayed and worked, and the total miles tested, are automatically computed. The format of the report file is predefined and is designed for transmission via a modem to a home office on a regular basis. In addition, a permanent record of the test results is maintained on a removable hard disk drive. The test data may be played back for review at any time, either in the test vehicle, or back at the home office at a later date as required. A facility for "dumping" the data on the screen to the printer is provided. This facility can, thus, provide a convenient method for obtaining the graphic presentations of recognized flaws in hard copy form.

Figure 3:
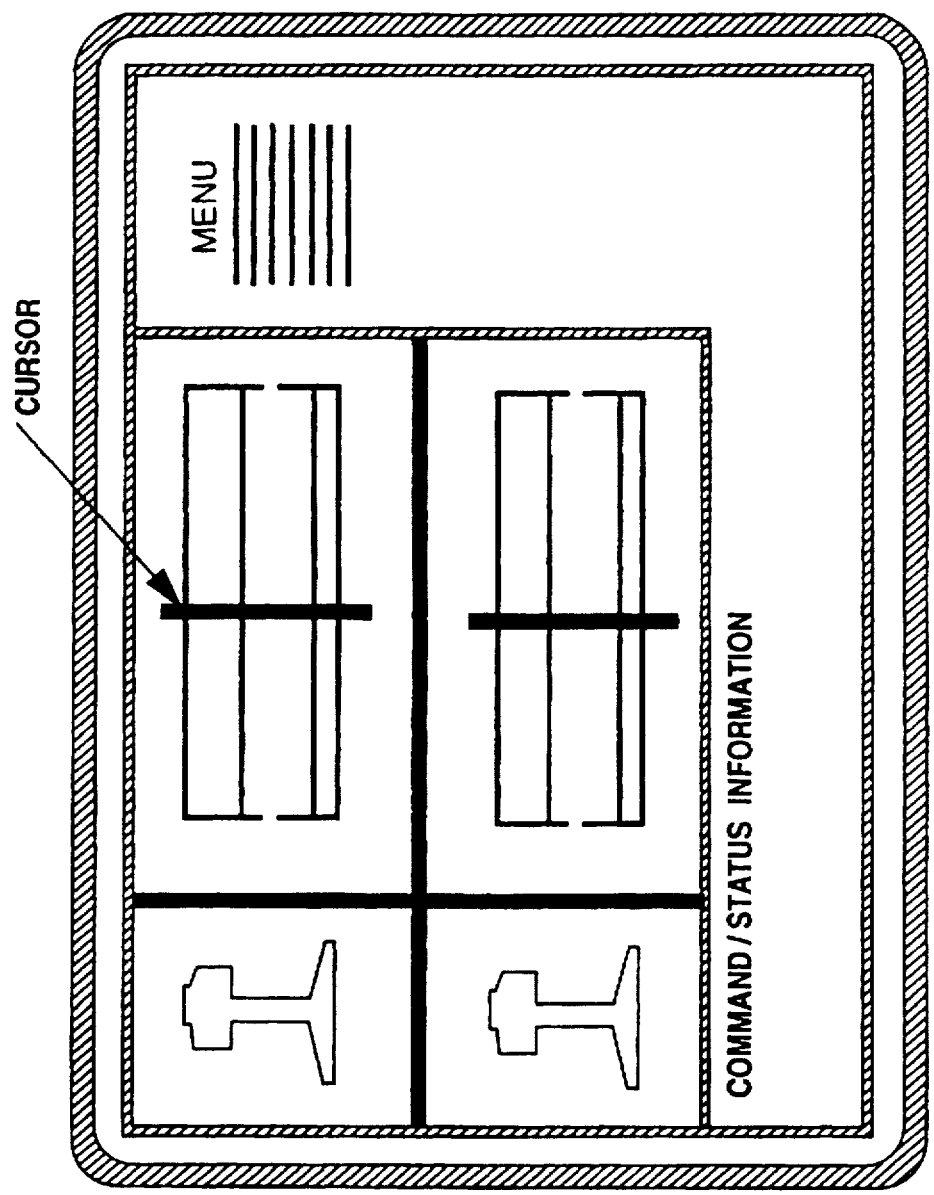
FIG. 3 illustrates a typical screen presentation for use with the invention.

The graphics and visualization sub-system can provide a graphic view of flaws as they are recognized, including three dimensions of information. These data can be reviewed by an operator to help verify the decision, and the presentation can be dumped on a printer. The presentation format, for real-time operation, is shown in FIG. 3. The operator is also provided with other presentation options. An automatic gain control (AGC) feature is used in the zero degree base channel amplifiers to compensate for fluctuations in signal strength of the reference signal (bottom of rail), caused by varying rail conditions. This facility occurs at all normal gain settings, and includes a mechanism to prevent gain surges when a flaw might mask the reference signal. A time corrected gain control feature (TCG) is used in the amplifiers to offset the attenuation factor of the signals in the steel. This feature is sometimes called distance amplitude correction (or DAC), and attempts to force defects of the same size to appear with the same signal strength regardless of their depth in the steel.

System verification is supported through the provision to the operator, in real-time, of a graphic representation of the data on which flaw detection decisions were made. This provision also allows rapid checks of basic functionality when test signals are applied at the system input. Also, several maintenance functions, which test the integrity of the system hardware components, are available.

The system hardware of the instant invention is divided into two major groups: a mechanical sub-system, and the electronics/computer subsystem. The mechanical subsystem consists of a carriage assembly containing the ultrasonic probes and associated hydraulic and pneumatic controls. Also, a mounting facility on one of the Hi-rail wheels for an incremental shaft encoder is provided.

The electronics and computer subsystem, FIG. 1, consists of the user interface computers (System Control Computer and the Graphics and Visualization Computer), and the Distributed Multimicrocomputer Flaw Detection and Recognition System. The user interface computers include color graphics monitors, touch sensitive screen and keyboard input, and a dot-matrix printer for hard copy report and graphics printout. The ultrasonic flaw detection equipment consists of nineteen inch racks of ultrasonic signal recovery and processing computers/electronics and four wheel probes. Two standard dual-channel oscilloscopes are also used for monitoring of the ultrasonic signals received from the wheel probe transducers.

The mechanics of the system hardware consists of the Probe Wheel Carriage assembly, which is a device designed to support and control ultrasonic probe wheels for field testing of railroad tracks. The carriage assembly makes extensive use of linear ball bushings which are supported in pillow blocks for each mounting. They allow smooth, accurate positioning and suspension of the probe wheels. The probe carriage runs on guide wheels and has controls to align the four wheel probes over the web area of the rail. When installed on a Hi-Rail vehicle, the carriage is raised into a well at the rear of the vehicle for protection while on the road or during transit.

The carriage assembly is designed with controls to aid the operator in maintaining alignment of the wheel probes over the web of the rail. The two probes on each rail are controlled by a common Cant and Lateral adjustment. The carriage also provides a mechanism for locking the carriage guide wheels to the gage of the rail to maintain the alignment set by the Cant and Lateral controls. The layout of the carriage and associated controls is shown in FIG. 4.

Figure 4:
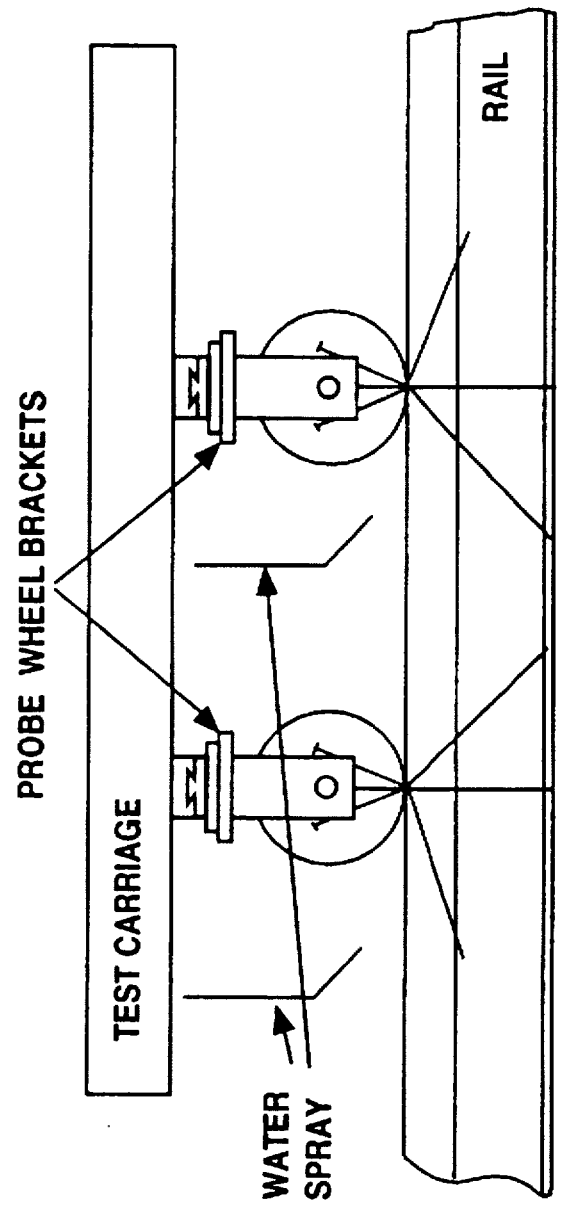
FIG. 4 illustrates carriage and wheel probe orientation.

The carriage is designed for quick replacement of the wheel probes in the event of a "flat tire" through a dove-tail bracket as shown in FIG. 4. Replacement of a probe requires loosening of a single screw. The wheel and wheel bracket assembly are removed and replaced as a single unit. Replacement and alignment of a wheel probe typically takes less than five minutes to complete.

Figure 5:
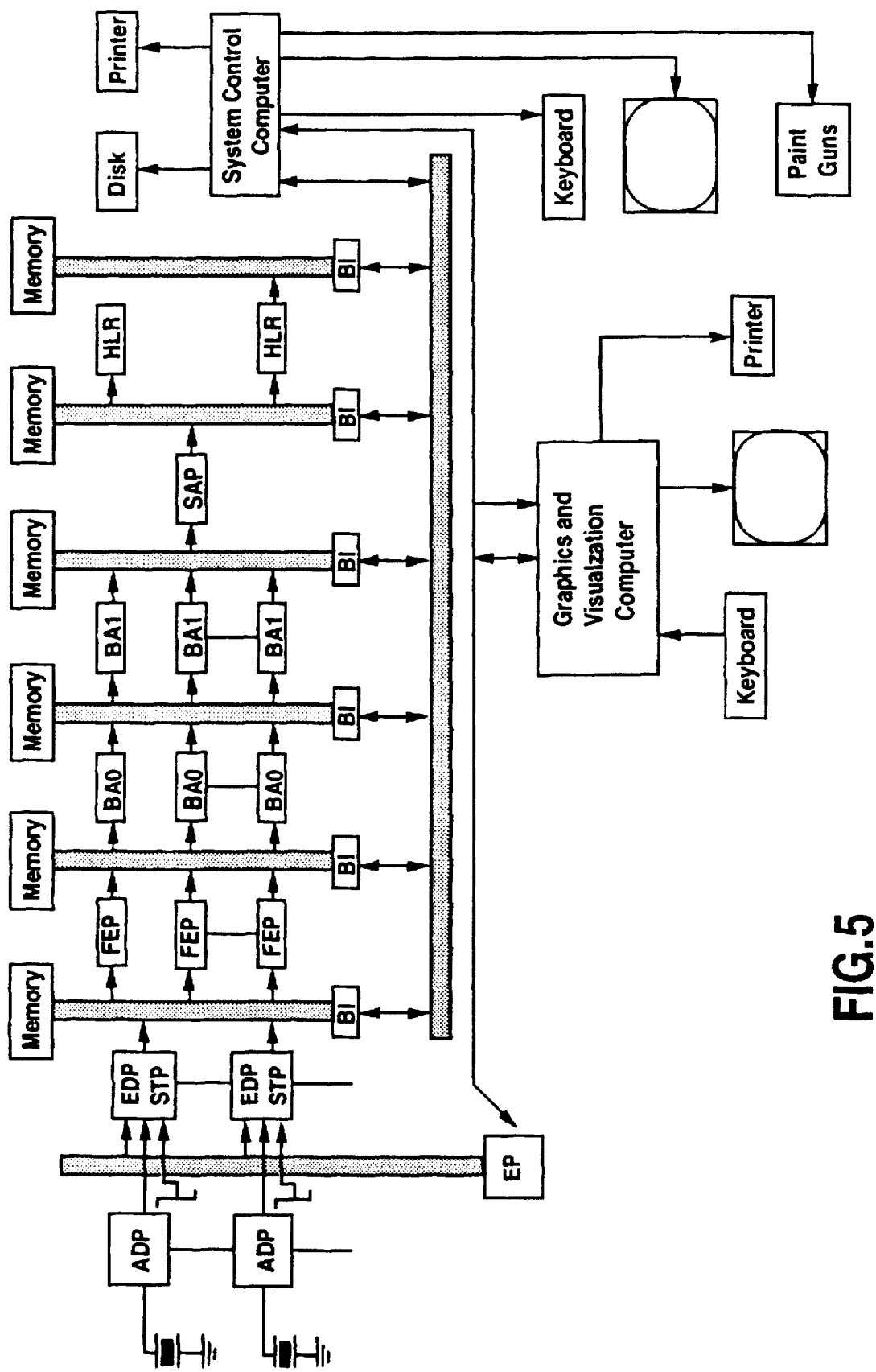
FIG. 5 is the computer organization utilized with the system.

A high-level block diagram of the computer and electronics configuration is shown in FIG. 5. A multiple processor, shared memory architecture is utilized to obtain maximum computing efficiency for a pipelined algorithm organization. The architecture utilizes a multiple sequence of microcomputer arrays, where each microcomputer has direct access of a shared memory with its predecessor processor to quickly access input data, and direct access of a shared memory with its successor processor to quickly deliver output results to the next stage. This architecture is unique, and provides a capacity to achieve a greater composite processing power and efficiency over other alternatives.

The analog and digital preprocessing unit (ADP), contains a remote pulser/amplifier, analog recovery electronics (including AGC, TGC), and digital recovery electronics, which filter the data and prepare a test report for the subsequent software processing stages.

There are seven subsequent software processing functions imbedded in the total system, as shown in FIG. 5 (EDP, STP, FEP, BAO, BA1, SAP, HLP). These functions carry out a sophisticated pattern recognition process to insure a high degree of flaw detection capability, and also provide visualization data for graphics presentation. The functions may be assigned to processing stages in the architecture, either in parallel (vertical) fashion to increase processing speed at that stage, or within a stage if the processing speed requirements of the application allow. Thus, the total quantity of "columns" of processing sections, and the total quantity of processors for a particular application, can be determined by the operator to fit the application performance needs. This approach can thus provide an ease in future upgrading of existing systems, as well as a capability of providing cost-efficient architectural solutions for applications that do not require extremely high amounts of processing power.

The environmental processor provides a system interface to the external parameters of the system by keeping track of rail position, vehicle velocity, and various event times that are important to reliable system operation. Thus, the rail position for each test report is made available to the software processing stages at the time when the test is carried out.

Ultrasonic non-destructive testing involves the use of ultrasonics to test a material such as the steel of a rail, without destroying the material in the test process. This technique relies on the ability of the ultrasonic vibrations to propagate through the material, and to reflect off of discontinuities such as voids or cracks in the material. Ultrasonics is the use of sound waves which have a frequency which is higher than an adult human is able to hear (greater than 20,000 cycles per second). In many ways, ultrasonic testing is similar to the use of radar or sonar, in that reflections of the sound energy can be used to detect or identify targets or "features". Just as a light beam will reflect off of a wall, a beam of sound energy will reflect off of a discontinuity in the medium (e.g. the material, the steel of the rail). In some instances, the reflection will be a normal rail feature, such as the bottom of the rail, a normal bolt hole, or a rail end. In such cases, the feature is considered "normal" and the reflection is not reported as an anomalous condition. The skill in ultrasonic testing lies in discriminating between normal features such as the bottom of rail, and abnormal conditions, such as voids in the rail structure.

If a beam of sound is sent directly into the rail (zero degrees from the vertical), it will be reflected off the bottom of the rail and an "echo" will be seen by the detection equipment. This is an expected condition and the lack of this expected response, termed "LER", is useful information since it indicates that either the sound beam has been obstructed by some other discontinuity, or that there is not adequate "coupling" of the sound energy into the steel. Another feature which is often detected, is a reflection from the underside of the head in the fillet area of the rail. The strength of this echo is highly dependent on the alignment of the test probe on the rail is useful in maintaining proper alignment of the equipment.

Many defects are oriented nearly vertically in the rail and often will not give a significant echo to the zero degree beam traveling vertically down through the rail. In order to detect these defects, it is necessary to use a number of directional beams at various angles, each looking for particular features in the rail. A beam of 45 degrees from the vertical detects cracks which propagate from bolt holes. A 70 degree beam detects transverse defects in the head area.

Accurate sizing of defects is important in order for the railroad to determine the severity of the defective rails. Due to the wide variation of the amount of sound energy transmitted into the rail caused by constantly changing conditions such as worn and rusty rails, grease on the rail, etc., the amplitude of reflected signal is not a useful characteristic to use. Transmissions of the sound beam are made at fixed intervals based on movement of the test vehicle. The equipment looks at the number of successive echoes received from a feature and uses this information to give an indication of the size of defects.

Figure 6:
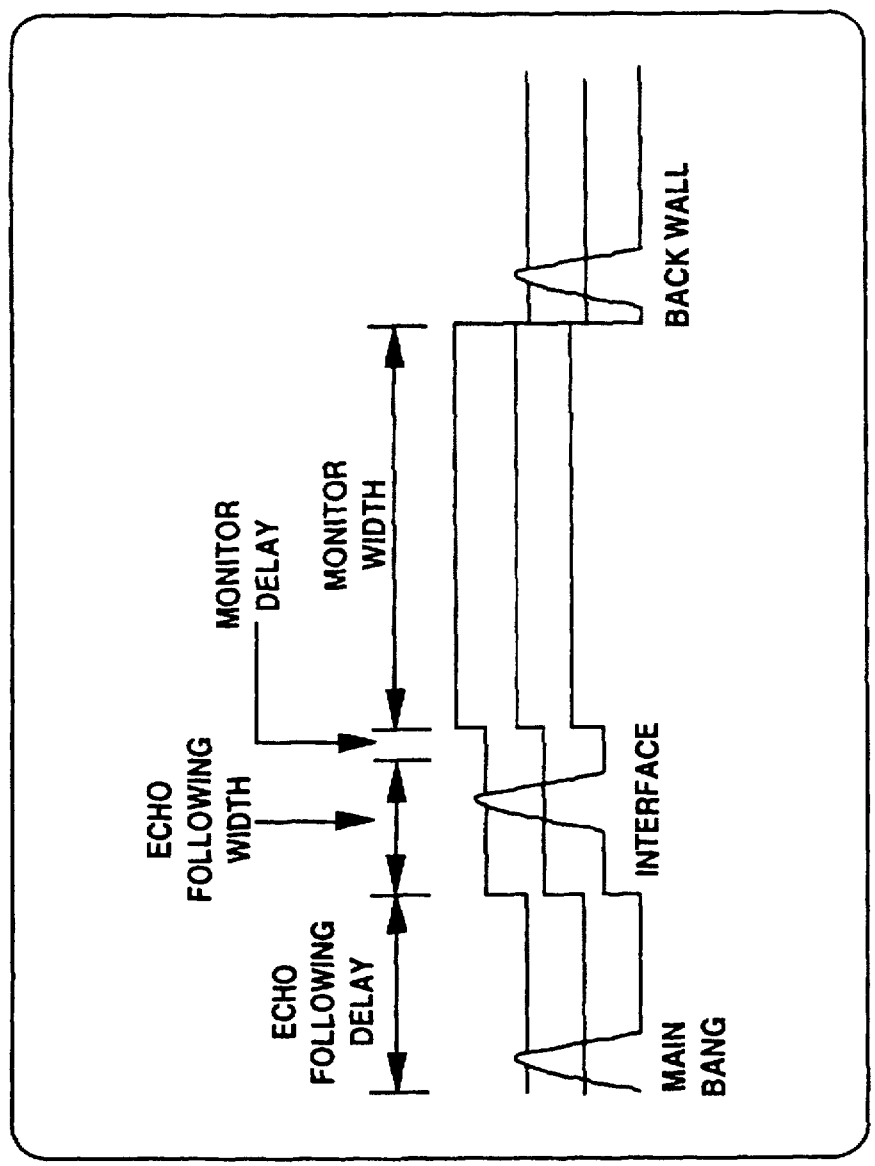
FIG. 6 is a typical ultrasonic waveform.

The transducers used with the instant invention are typically centered at 2.25 Mhz in frequency, and are located in fluid-filled wheel probes. The transducers transmit the high frequency sound vibrations into the steel of the rail, and are then used to "listen" for return echoes from discontinuities in the steel. The wheel probes which house the transducers are essentially designed to provide the proper acoustic properties needed to maximize the amount of sound energy transmitted into the steel. In addition, a water spray on the surface of the rail is needed for adequately coupling the sound energy into the rail. FIG. 6 illustrates typical signals seen in a rail when using a zero degree beam. At the left of the figure is a picture of the physical signal path which the energy takes. The right side of the figure shows the ultrasonic echoes as they would be seen on the ultrasonic display.

The first signal which occurs is the transmission of the beam (E). This is called the excitation pulse and occurs when the transducer is "hit" or "fired" with a high voltage (typically 300 Volts) electrical pulse. The electrical energy is transformed into vibrations which are sent into the fluid in the wheel. The time it takes for the sound to travel from the transducer to the rubber membrane in the wheel is called the water path (W). The signal then travels through the rubber membrane, and into the steel. Depending on the amplifier gain in the system, one of two echoes will be seen at the surface (S). If the gain is high, the two echoes will normally be seen as a single echo as illustrated.

The number of echoes which appear after the surface echo (S), varies with the different transducers contained within the wheel probe. In the illustration of the zero degree beam, there are several echoes between the surface echo (S), and the echo from the bottom of the rail (B). The largest of these echoes (F), is from a discontinuity in the steel (e.g., an anomaly or flaw), which is near the center of the web area. Note that in this case, the flaw artifact only partially blocks the beam of sound energy from reaching the bottom of rail. In instances where the bottom of rail echo is completely obscured, and there is then a failure to detect it, the system generates a Lack-Of-Expected Response (LER) alarm. This information is important to the operator, since it implies that either there is a defect which is masking the echo, or that there is a potential equipment problem which must be investigated.

The transducers which transmit sound into the steel at an angle (the 38 degree and 70 degree channels) do not have a bottom of rail echo since they are not aimed at right angles to the bottom of the rail. The signal strength of the surface echo is also reduced for the same reason.

Because of the wide range of orientations of defects which occur in the rail, the System uses several different beam patterns which are at different angles in the steel to provide maximum coverage. Four identical wheel probes are used, two for each rail. Each is interchangeable, and contains a zero degree beam, a 70 degree beam, and a 38 degree beam. An optional 40 degree side looking transducer is also available. The two wheels on the same rail are oriented 180 degrees from one another as shown in FIG. 2.

The zero degree longitudinal wave beam (3.5 MHz), is used to detect horizontally oriented defects such as split heads and webs, and for detecting cracked or elongated bolt holes. It also detects many vertical split heads. This beam is directed normal to the rail running surface, penetrating through the web to the rail base. It will also detect any defect which masks the bottom of rail echo. The zero degree beam is also used to give an indication of rail height and provides the primary means of aligning the wheel probe over the web of the rail. The echoes from zero degree transducer are routed to two independent data processing channels, one for flaw detection between the surface and bottom of the rail, and one for monitoring the bottom of rail echo.

The 70 degree shear wave beam (2.25 MHz), searches the head of the rail and the top of the web area. It is primarily used to detect transversely oriented defects such as TD's and for defective welds, and is also useful in detecting vertical splits in the head area. The two probe wheels provide two shear waves at 70 degrees from the vertical in each rail in opposite directions; one aimed in the forward direction, and one aimed in the rearward direction.

The 38 degree shear wave beam (2.25 MHz), is mainly used to test the web area of the rail for cracked bolt holes, welded rail joints and piping in the web area. These probes may also detect peculiarly aligned transverse defects missed by the 70 degree transducers. The two probes provide two shear waves at 38 degrees from the vertical in the rail in a pitch and catch mode; one aimed in the forward direction, and one aimed in the rearward direction.

An optional set of 40 degree shear waves (2.25 MHz, not shown) aimed at the field and gage sides of the rail (thus, called side looking) are available. These channels are used mainly for testing for vertical split head defects.

Figure 7:
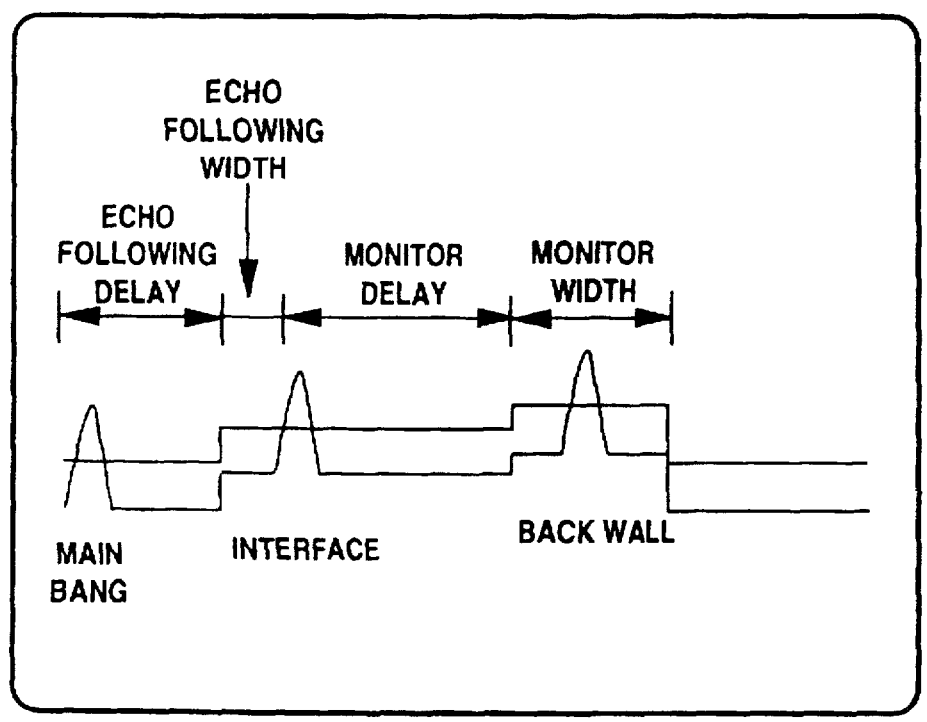
FIGS. 7 and 8 show the response from a zero degree base channel.
Figure 8:
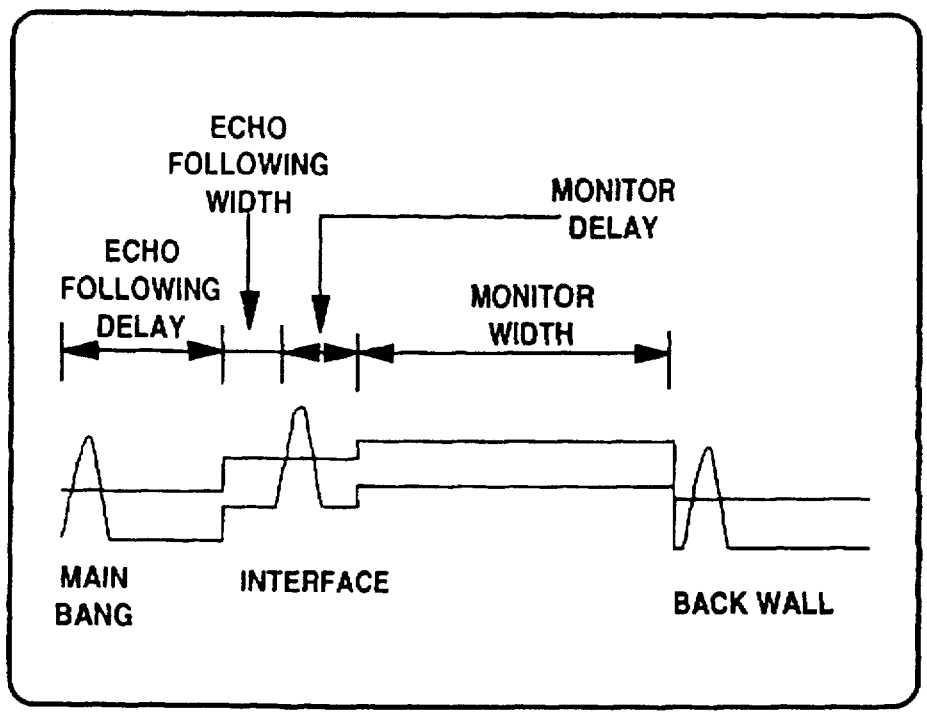

In ultrasonic testing, only part of the ultrasonic signal waveform is actually of interest and needs to be processed for flaw detection. In particular, only the signals received after the surface echo, out to some maximum distance in which defects might occur, are of interest. In setting up the system, the operator sets individual "monitor gates" for each of the transducers in the system. In addition to selecting a particular period of time in which to process echoes, it is also desirable to be able to eliminate echoes which are below a threshold. The gating and the threshold levels are generated by the Digital Preprocessor Module. FIGS. 7 and 8 show typical waveforms for the two channels used to process signals from the zero degree transducer. As can be seen in the diagrams, both the location of the gate and the threshold level are superimposed on the ultrasonic waveform.

In the case of a flaw detection channel, the monitor gate begins just past the surface echo. The length of the gate will depend on the individual channel. In the case of the zero channel, the monitor gate ends just before the bottom or rail echo. In LER (Lack of Expected Response) channels, such as the Zero Base channel, the monitor period is set such that the expected echo (the bottom of rail echo) is centered within the gate.

The ultrasonic signals which occur within the monitor gate area are compared to the threshold level. If an echo exceeds the threshold, the transit time corresponding to that echo is loaded into a FIFO (First-In First-Out) register in the Digital Module. Up to sixteen echoes can be detected with each gate. The resolution of the transit time is operator selectable to a resolution as fine as ten nanoseconds. The measured transit times are directly proportional to the depth of the indication in the steel.

The reference point for all transducers within a wheel is set at the surface via "echo-following" logic. This logic tracks the surface echo such that the monitoring time is always at the same location within the steel of the rail. The signal from the zero degree transducer is used to generate the echo-following signal.

In order to aid the control and reduction of false alarms and missed detections, the system applies several stages of hardware and software processing. To help remove "expected" noise, both a fixed baseline threshold and an additive, software applied timevarying threshold pattern is utilized. This technique can help avoid interference from system receiver noise, and spurious responses which might come from undesirable underhead reflections, etc.

Correlation of multiple channels (transducer) data, based on studies of expected response patterns for different flaw categories, is used to aid the selection/rejection of other "unexpected" responses that do not relate to the desired detection process for a particular flaw category. This process is carried out as a feature extraction process.

Figure 9:
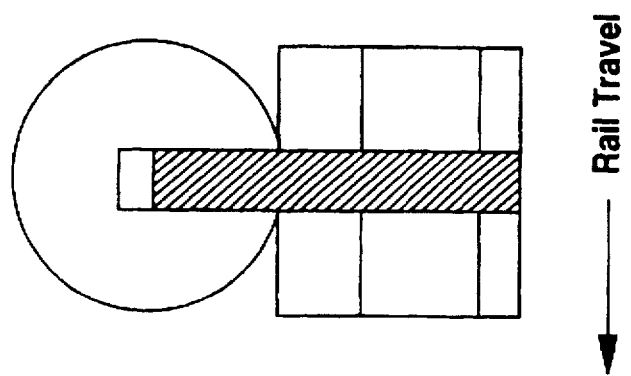
FIG. 9 illustrates the system's multiple look at a typical defect.

The system also uses a volume count system to establish anomaly alarm and reset counters to provide further correlation of position to position response data. Only if a feature volume (e.g., size) exceeds a minimum count (e.g., successive position tests) will a further indication of that anomaly be processed. The system looks at "slices" of rail and combines slice information in a 3-D context to evaluate total anomaly volume. The maximum resolution of the analysis is $\frac{1}{16}$th of an inch. Since the sampling resolution is less than the width of the sound beam in the steel, even small anomalies will be seen over more than one test cycle (FIG. 9). Equally important are the dimensional thresholds for the x,y,z positions around a particular anomaly of interest. Only if an indication has not been seen for dx, dy, and dz distance thresholds about the anomaly, is the volume count determined (e.g., a reset of the anomaly detection process). Thus, missing data points caused by noise variations, can be accounted for and the missed detection problem is alleviated.

Finally, the high level pattern recognition process further examines each detected anomaly's context in the rail, to be sure that it is not part of an expected pattern (e.g., bolt hole, etc.).

Figure 10:
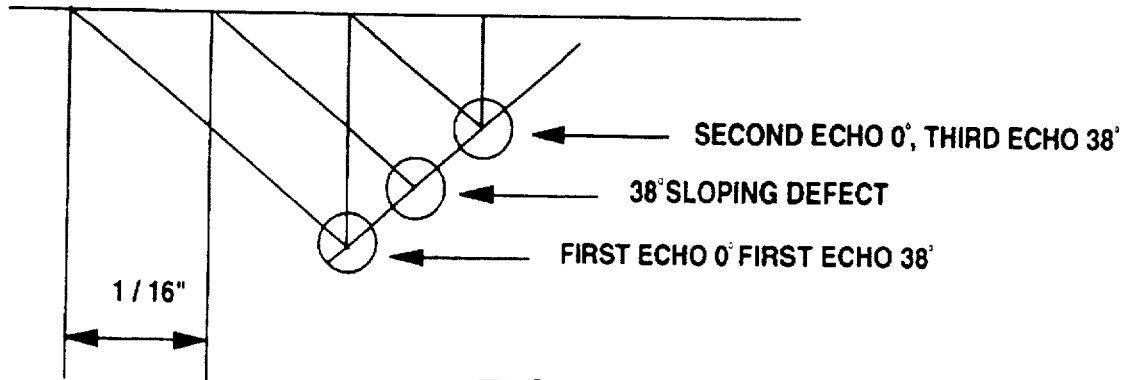
FIGS. 10A and 10B are illustrations of angle beam echoes versus distance travelled.
Figure 10:
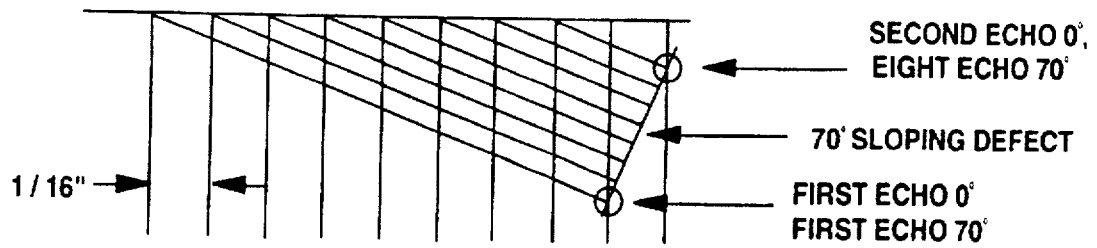

Note that the actual number of echoes for each positional reference point varies with the angle of the transducer's sound beam, the vertical orientation of the defect and the size of the defect. This is shown in FIG. 10. The vertical orientation of the Y defect is assumed to be at right angles to the path for maximum signal reflection. In this case, there are two 38 degree echoes for each increment of position as compared to the zero degree case where there is a one to one correspondence. Similarly, there are eight 70 degree echoes for each increment of position. The length of a defect can be approximated using this information along with the flaw counter data presented to the operator. The following table lists the approximate correlation between the flaw count and the flaw size:

| Channel | Size |
| --- | --- |
| 0 degree, 40 degree | .063" |
| 38 degree | .045" |
| 70 degree | .021" |

In the area of real-time detection and pattern recognition for non-destructive test applications, it has become necessary to manage ever increasing data rates, while also achieving higher resolution and more sophisticated pattern recognition. These two needs create contention in system resources, since higher data rates demand shorter processing times to achieve the needed functions, while higher sophistication and resolution demands longer processing times. Current single processor systems are unable to meet these needs effectively. The system described here has been developed to resolve this problem. A hierarchial approach is used to distribute the total pattern recognition task into a set of stages in which the recognition at one stage provides input results for the next stage. The stages are defined in a manner to accommodate essentially all aspects of the pattern recognition problem, and also to relate directly to a pipelined, distributed processing architecture. This allows the total pattern recognition task to take advantage of distributed processing hardware to achieve real-time operation effectively in a sophisticated format which is not possible with other approaches.

What is most unique about the approach is the integration of several types of recognition activity in a single structure with a format that provides for smooth, extremely high speed operation. A description of the approach is given below.

Figure 11:
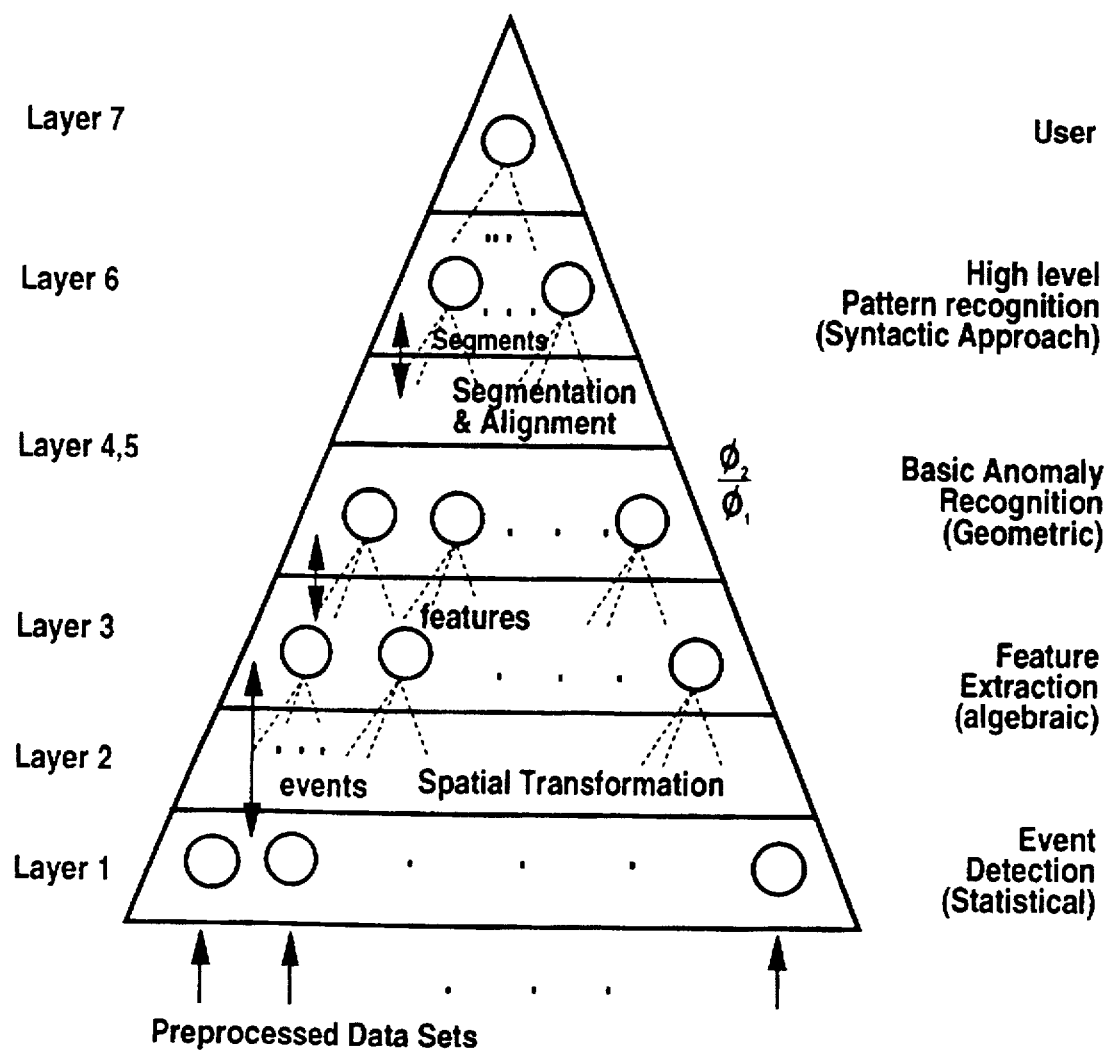
FIG. 11 illustrates the system's pattern recognition system.

The hierarchial, pipelined, pattern recognition system depicted in FIG. 11 shows a multi-layered structure, where each layer carries out a specific aspect of the total pattern recognition task. These levels are:

a. Event Detection (statistical decision theory);

b. Spatial Transformation (geometric mapping);

c. Basic Anomaly Recognition; and d. High Level Pattern Recognition (automata theory, context analysis, artificial intelligence).

Each of these levels implements a function which is commonly found in one or more pattern recognition approaches; however, the instant invention is able to integrate the set of activities in a composite recognition system suitable for real-time, distributed applications. At each stage, the complexity level of the sub-task becomes greater; however, also from each stage the raw data rate is correspondingly reduced due to the ability to send along only that information relevant to the next stages. Thus, data is selected, compacted, and represented at each stage in a manner that enhances the efficiency of the system. In that manner, only the first stage must really keep up with a potentially enormous incoming data rate; the subsequent stages experience decreasing input data rates as the relevant information is extracted from the arriving data samples. Each stage is intended to be mapped onto a distributed, pipelined system such that each system has the same utilization. Also, each stage must be buffered (queued) to accommodate the normal fluctuations in execution time that occur in each stage due to the data content/processing.

Figure 12:
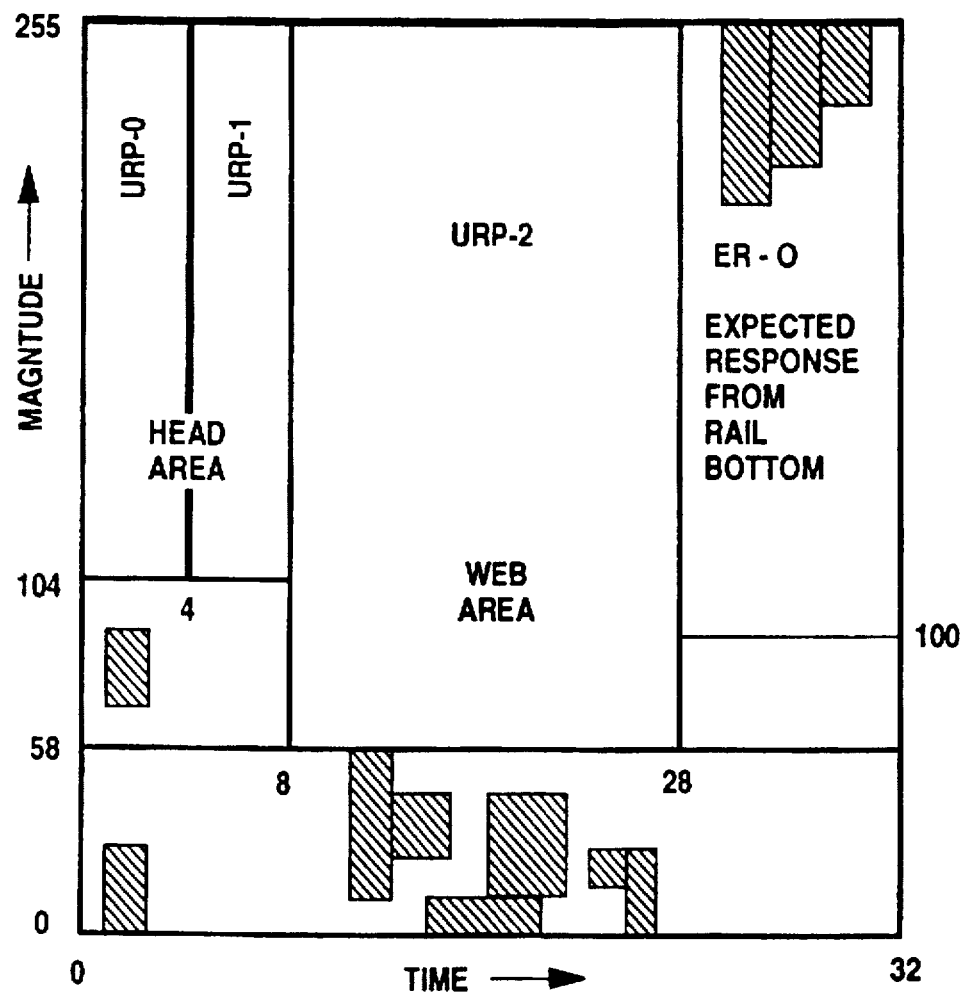
FIG. 12 shows a chart of event detection.

The event detection stage applies statistical decision theory to the recognition of anomalies in the input data stream that (may) have relevance in the recognition process. This is done by using estimates of the probability density functions or normal responses and known (expected) anomalous responses, and applying statistical decision theory (e.g., Bayesian decision regions) to establish the occurrence of events of relevance. The inventive implementation uses 2-dimensional space to do this. There are two primary classes of information-bearing events: unexpected responses (URP); and lack of expected responses (LER). For each class it is desirable to retain as well the typifying input data properties (e.g., magnitude, quantity of samples, etc.). Other input data relating to expected responses and not pertinent to the user-selected decision regions is discarded. FIG. 12 illustrates a 2-dimensional decision region showing possible URP's for a zero degree channel.

Figure 13:
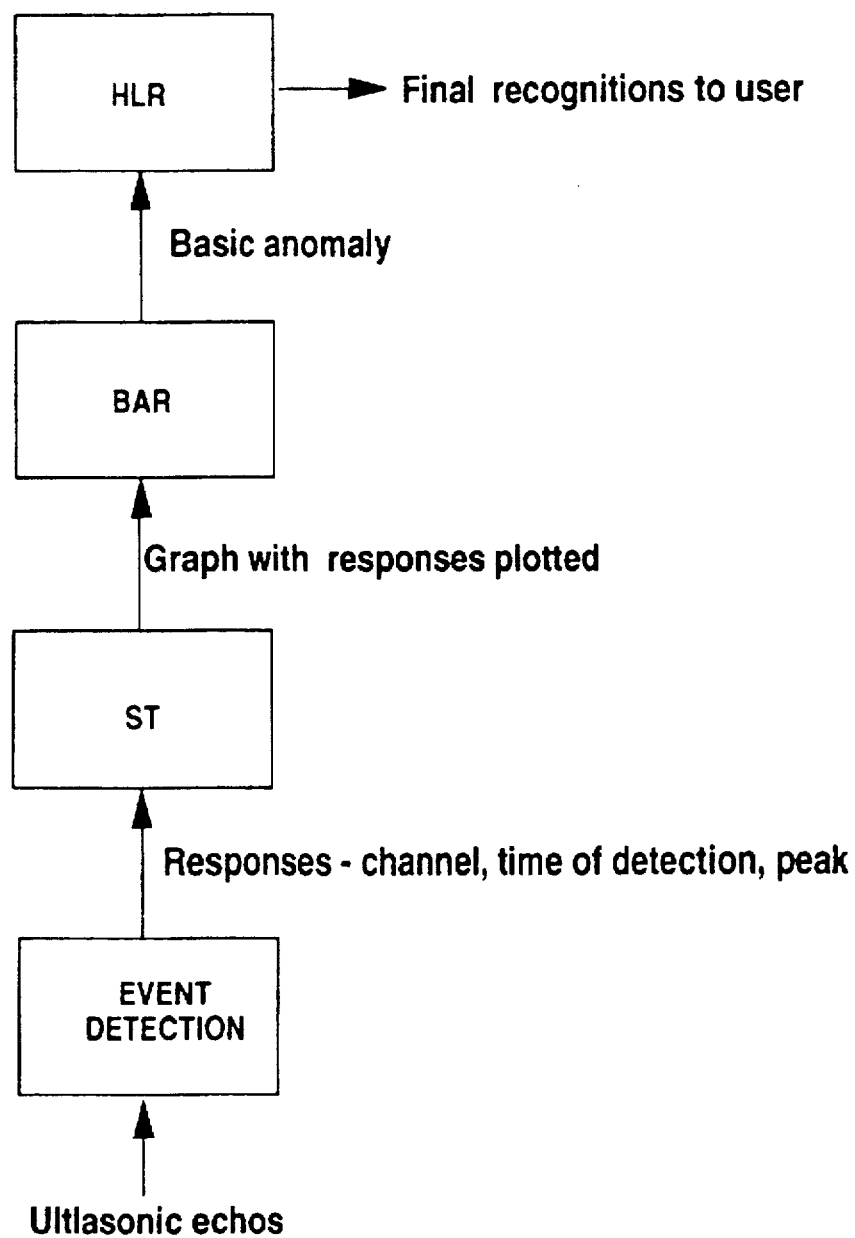
FIG. 13 is a flow chart of the pattern recognition system.

There are three stages in the recognition process following Event Detection (see FIG. 13). The first stage is called SPATIAL TRANSFORMATION (ST). During ST, responses from different transducer channels are plotted on a graph of the text piece.

The next stage is called BASIC ANOMALY RECOGNITION (BAR). The BAR stage scans the graph of the test piece produced by ST, and uses a grouping approach to recognize simple flaws patterns such as bolt holes and surface cracks.

The last stage of the recognition process is called HIGH LEVEL RECOGNITION (HLR). The HLR stage looks at a series of basic recognitions and matches it to patterns stored in memory. The HLR stage has the ability to distinguish between flaws in the test piece (such as a cracked rail), and normal patterns that are picked up by the ultrasonics (such as the junction of two rails). This process is done automatically and in real-time, thus eliminating hours of idle time required for operator interpretation of responses.

Figure 14:
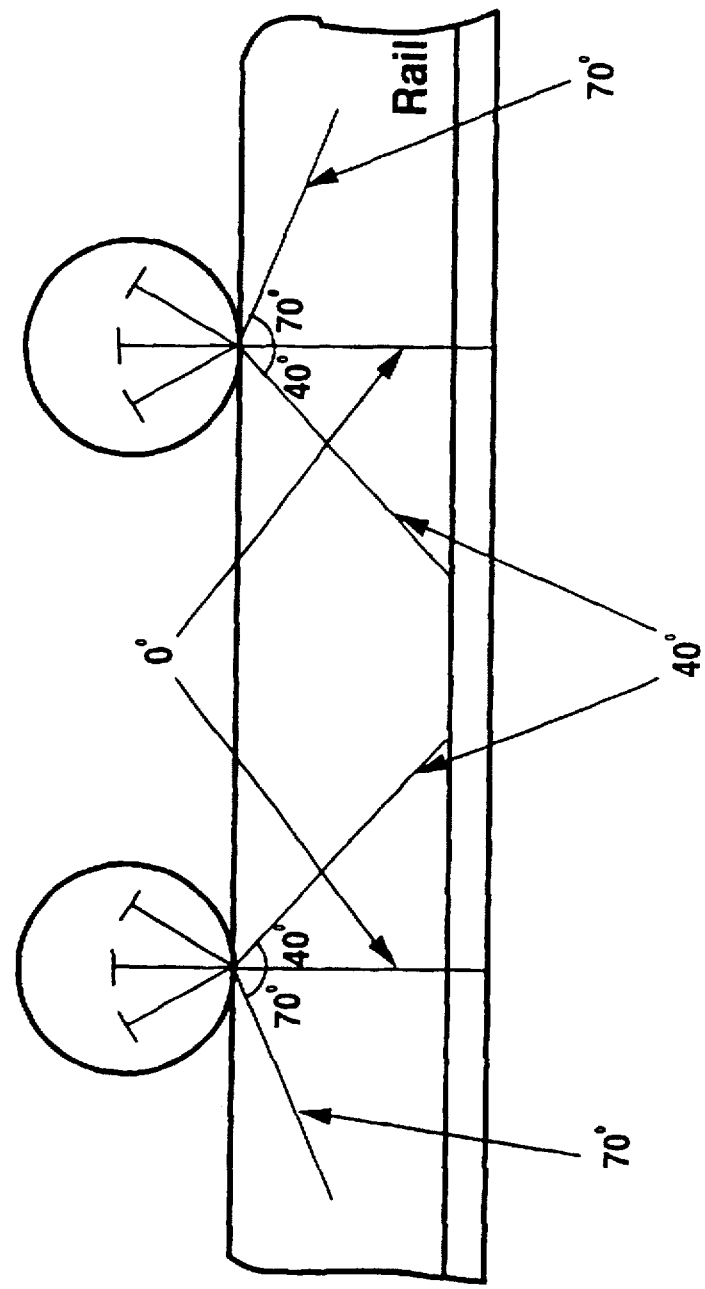
FIG. 14 illustrates a second example of transducer orientation; FIG.
Figure 15:
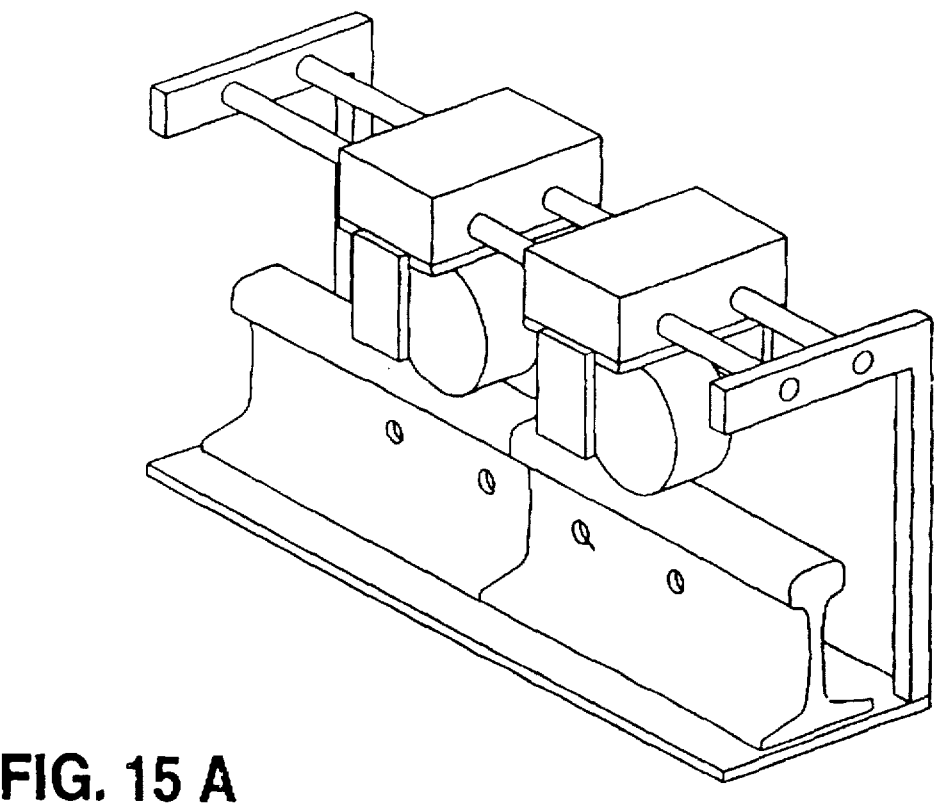
FIGS. 15A and 15B show the point of reflection for ultrasonic signals.
Figure 15:
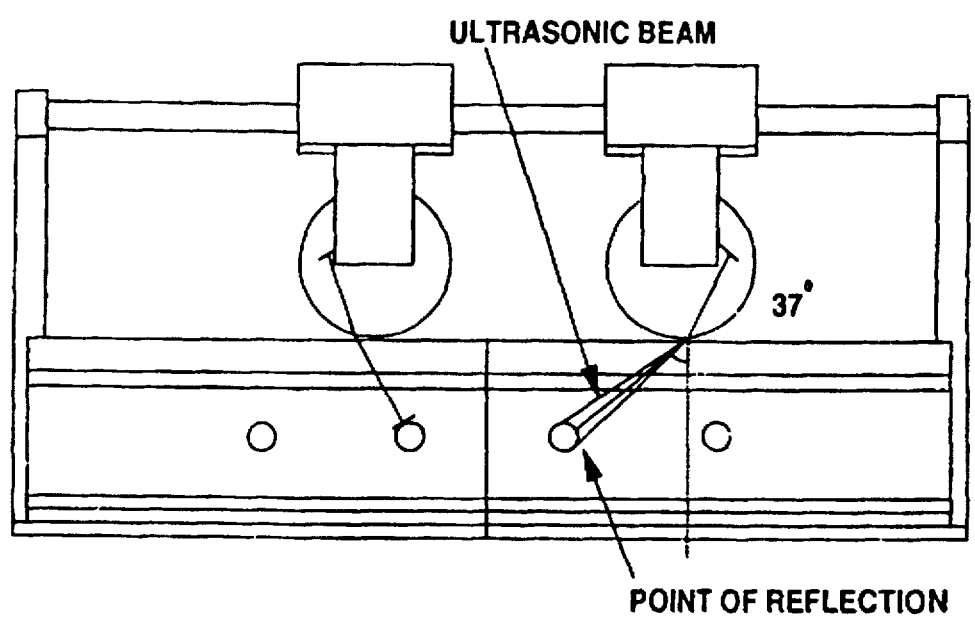

During ST, responses from different transducer channels are plotted on a graph of the test piece. FIG. 14 shows the orientation of the transducers in the testing wheel. In order to plot the responses, the ST stage must compute the path travelled by the ultrasonic beam. The end point of this path will be the position at which the ultrasonic beam is reflected off the flaw. The position is a function of the following variables (See FIG. 15):

1) Angle of travel of the ultrasonic beam;
2) Speed at which the beam travels through the material;
3) Position and orientation of the transducer;
4) Beamspread as ultrasound travels through material;
5) Delta travel time of the beam in the test place; and
6) Strength of the ultrasonic response.

Variables 1, 2, 3 and 4 are fixed for a given channel and a given test material. Variables 5 and 6 are reported by the front end hardware of the test equipment for each transducer response. To perform the ST, the software takes each response, extracts the source channel and the travel time, and computes the flaw position and size using the beam model shown in FIG. 15.

Figure 16:
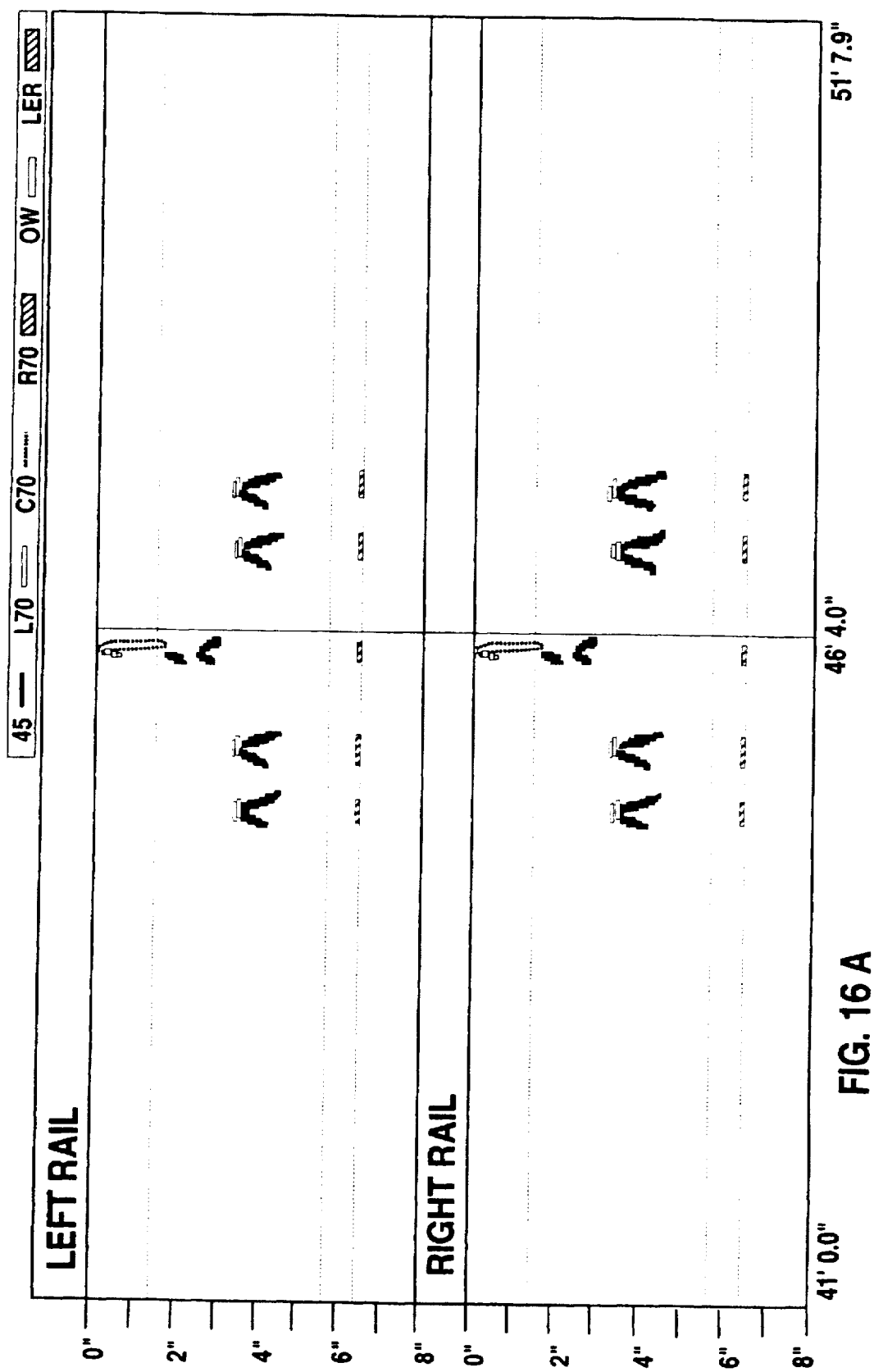
Figure 16:
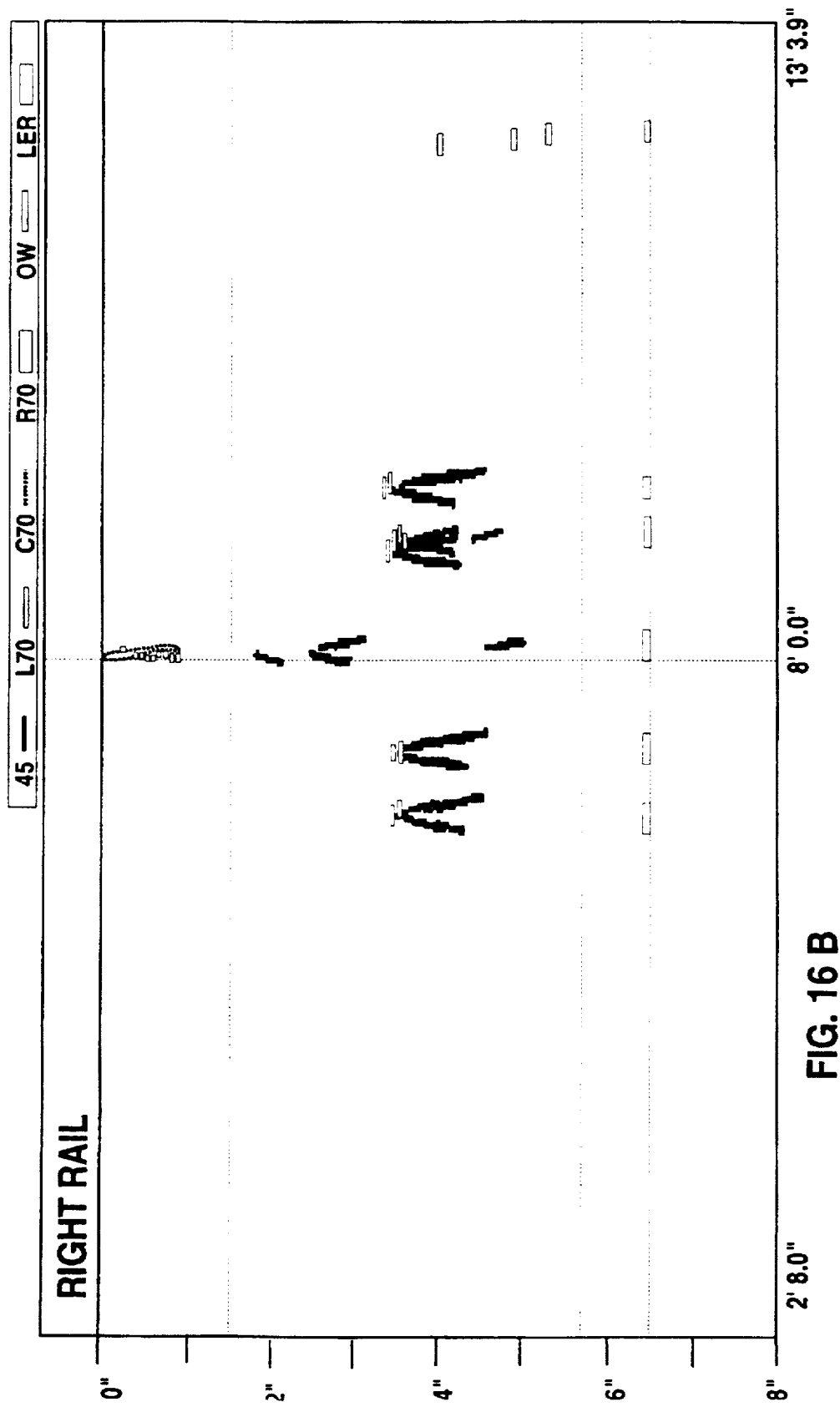
Figure 17:
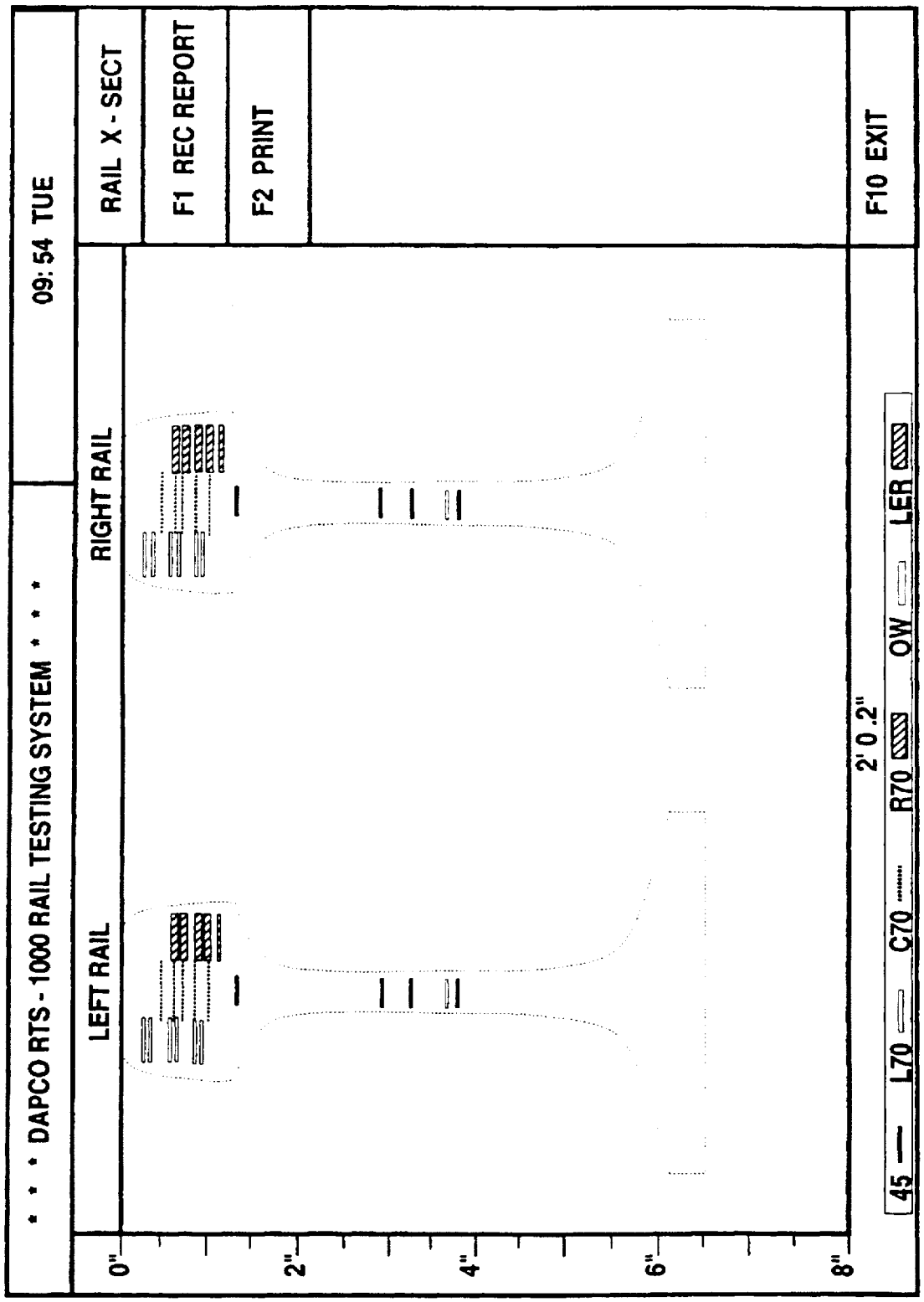

Once the position is found, the position is plotted on the CRT screen in a different color for each different channel. The plot consists of 2-D graphical representation of the test piece, which is updated in real-time. The test piece can be shown in profile or cross-section views (see FIGS. 16 and 17).

Figure 18:
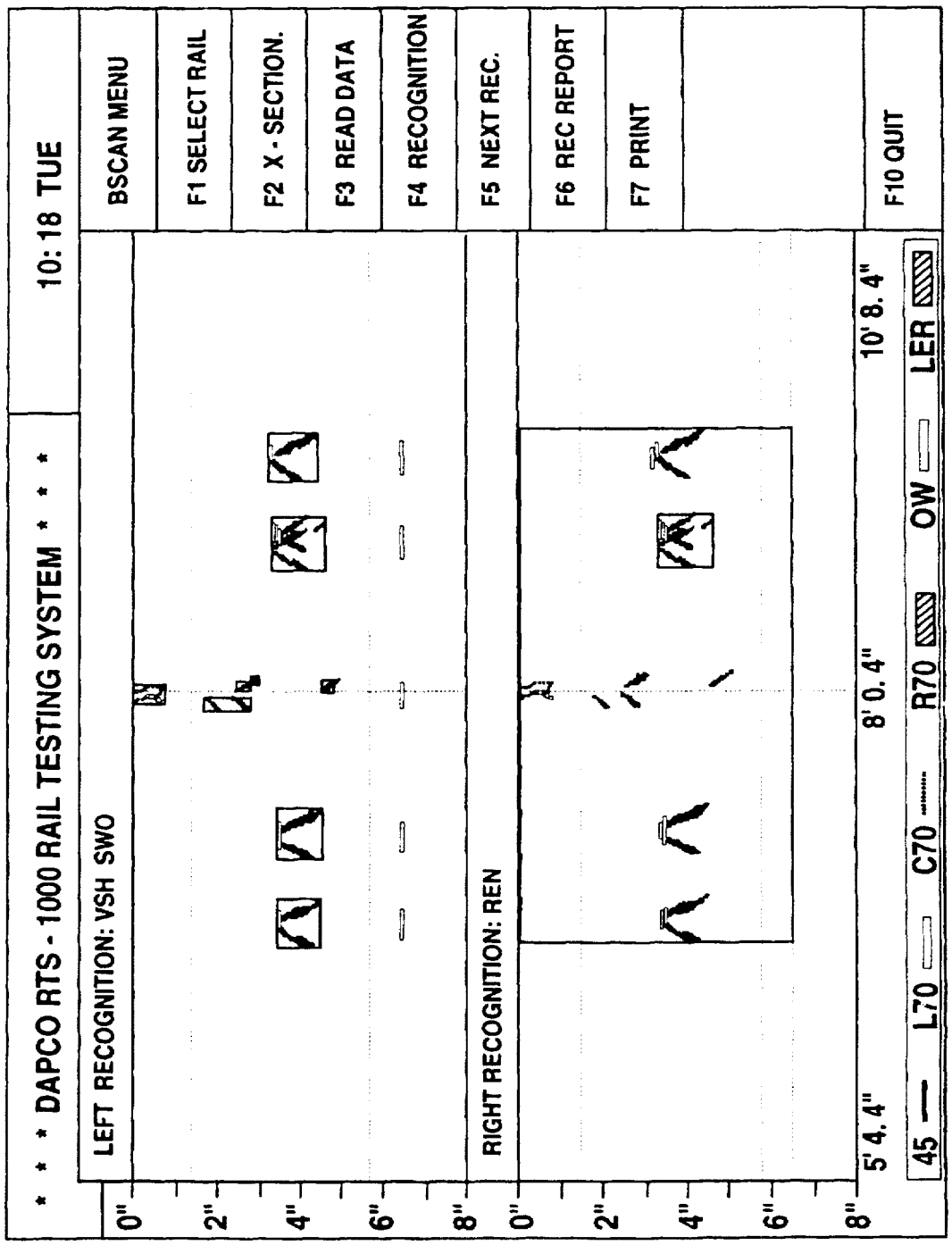

The Basic Anomaly Recognition (BAR) stage scans the graph produced by ST and uses a grouping approach to recognize simple flaws patterns such as bolt holes and surface cracks. To perform the recognition, the BAR stage scans the ST graph for sets of responses which are grouped together (see FIG. 18). Each group of responses is merged into a single chunk called a basic anomaly. The grouping of the responses is a function of the depth, channel and proximity of the responses to each other. By defining different depth and channel combinations, the BAR process can recognize simple flaw patterns that are always spatially correlated such as bolt holes, engine burns and surface cracks.

The last stage of the recognition process is called HIGH LEVEL RECOGNITION (HLR). The HLR stage looks at a series of basic recognitions and matches it to a pattern stored in memory. The HLR stage has the ability to distinguish between flaws in the test piece (such as a cracked rail) and normal patterns that are picked up by the ultrasonics (such as the junction of two rails). Since this is done automatically in real-time, there is no longer any need to stop the test equipment and manually verify the source of ultrasonic responses.

The HLR stage has the ability to recognize patterns which have very complex positional and grammatical/syntatic characteristics. The HLR stage works by scanning the stream of basic recognitions and matching them to patterns stored in memory. Each pattern consists of grammar which defines the sequence of basic anomalies that must be encountered to recognize the pattern. The pattern must also match a set of user definable positioning requirements. The positioning requirements specify the relative position of each basic anomaly to all others in the pattern. The output of the HLR stage is a listing of each of the recognitions which were made. Each recognition listing contains the following information (see FIG. 19):

1) Depth range of the recognition;
2) Length and position of the recognition;
3) Text string giving description of type of recognition; and
4) Indication of whether pattern represents a flaw in the material or a normal set of responses.

Figure 20:
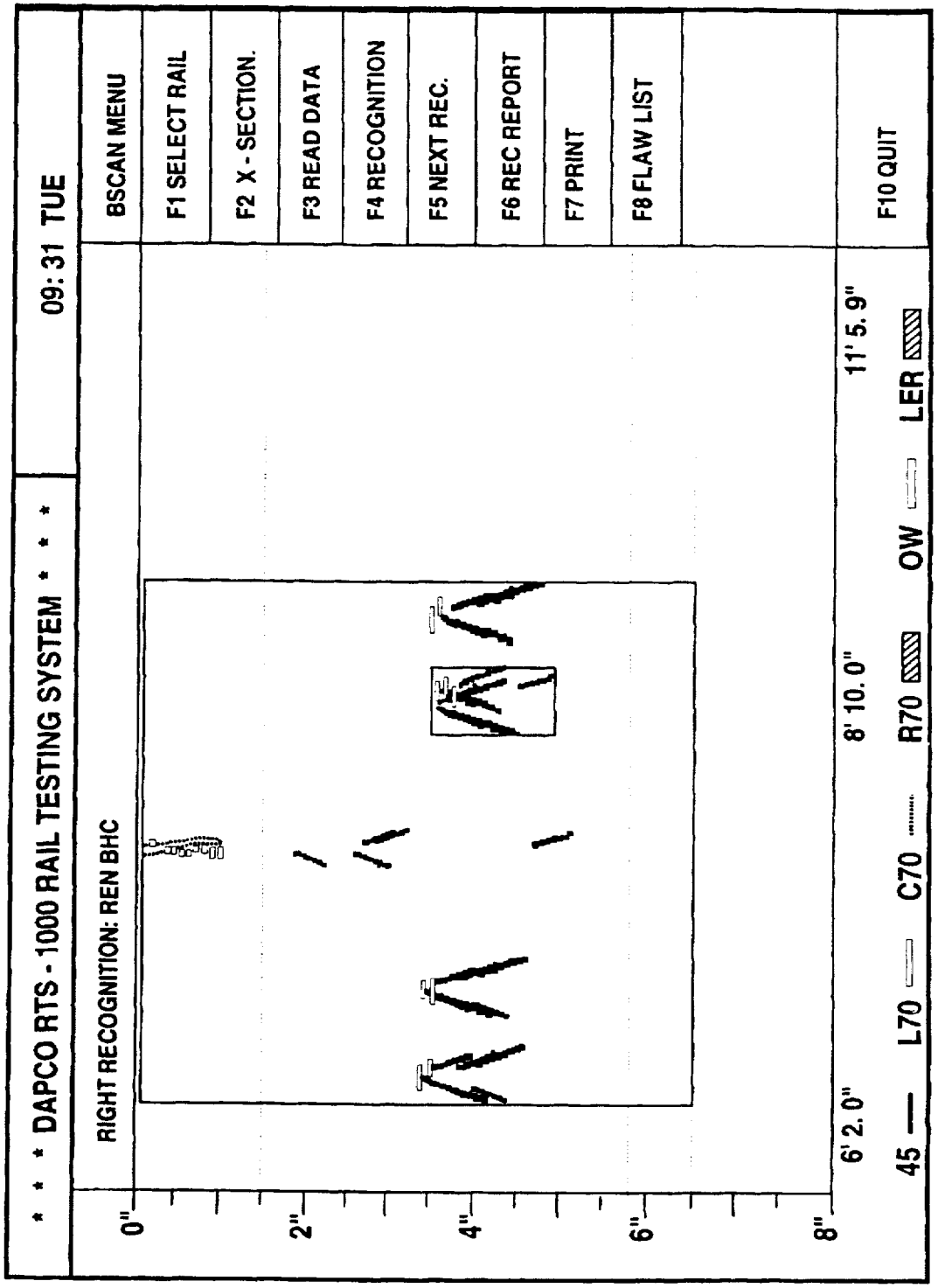

The HIR stage will also display a box around each pattern in the graphical display of the test piece and its corresponding description (see FIGS. 19 and 20).

There are three types of CRT displays in the system. The first display is the color monitor attached to the System Control Computer (SCC). This display is used to control the operation of the system and consists of a set of functional menu screens. The menu screen is used by the operator in determining the descriptive properties/parameters associated with a particular anomaly that has been determined to be a flaw.

A second display, a color graphics monitor, provides a means of viewing the data sets associated with a particular flaw, to aid in the verification process. Other optional presentations are also possible, such as a video version of a strip chart recording device. The data from this display is stored on a removable Bernoulli hard disk and serves as a permanent record of the test. The operator may stop the system and replay an area of rail, while verifying whether an indication is a defect or normal feature such as a rail end. The operator may annotate the data in the display using built-in codes.

Two standard dual-trace oscilloscopes provide the operator the ability of simultaneously monitoring the ultrasonic waveforms for any four transducer channels. At vehicle speeds below three MPH, the system automatically switches to a fixed repetition rate of 1 KHz. This provides ultrasonic waveforms at slow vehicle speeds which the operator may monitor to visually verify indications as defects. Many defects can be easily verified on the oscilloscope display without the need of hand-testing with a portable flaw detector instrument.

An optional paper-tape strip chart recorder may also be added in place of the graphics/visualization system. Recording is accomplished by pressure of black ink onto a four inch wide blank paper. The speed of the chart recorder paper drive is a synchronism with and controlled by the system incremental shaft encoder mounted on the right rear Hi-Rail wheel. In addition to indicating feature detections from the ultrasonic data channels, a position marking pen marks the tape at regular intervals which are operator selectable.

Maintaining proper alignment of the wheel probes over the web of the rail is extremely important in order to achieve reliable rail flaw detection. Misalignment may result in either missed detections, many false indications from the fillet area between the head and web, or both. The system carriage contains adjustments of both Cant and Lateral position of the wheel probes on each side of the carriage using controls mounted on the operator's table. One of the primary indications of correct alignment is the strength and tracking of the bottom of rail echo from the zero degree transducer. The operator is notified that a loss of base signal has occurred by the LER response on the CRT display.

The foregoing disclosure and description of the invention is illustrative and explanatory thereof, and various changes in the size, shape and materials, as well as in the details of the illustrated constructions, may be made within the scope of the appended claims, without departing from the spirit of the invention.

We claim:

1. A method for examining railroad rails for flaws using ultrasonic investigation techniques and for identifying flaws in the rail on a real-time basis, comprising the steps of:

repetitively and regularly injecting pulses of a plurality of ultrasonic beams into the rails from test devices mounted on a vehicle traveling along the rails, and detecting within the test devices acoustic echoes caused at rail discontinuities by the ultrasonic-beams to produce electrical signals representative of the magnitude of the acoustic echoes;

determining travel times of the acoustic echoes to the place of injection into the rails of the beams which caused the acoustic echoes;

while said ultrasonic beams are repetitively and regularly injected into the rails, deriving from said travel times, angles of travel, beam pulse speeds, and beam spreads of the ultrasonic beams inside the rails, spatial signals representative of the locations of the discontinuities along the rails;

combining spatial signals located within slices of the rails to identify and locate flaws in and along the rails while said ultrasonic beams are repetitively and regularly activated including the steps of storing information representative of normal patterns of known rail discontinuities and manufactured contexts, comparing combined spatial signals with said stored information to detect and identify unknown discontinuities and to one of eliminate and reclassify those discontinuities inconsistent with recognized context; and indicating the locations of said rail discontinuities.

2. The method for examining railroad rails as set forth in claim 1 wherein said combining step further comprises:

determining depth inside the rails of a discontinuity and the ultrasonic beams which caused echoes therefrom;

grouping spatial signals related to said discontinuity; and deriving from said grouping a basic anomaly recognition of spatially-correlated flaw patterns comprising bolt holes and surface cracks.

3. The method of claim 2, wherein said combining step further comprises the steps of:

storing a plurality of patterns which consist of a grammar requirement defining a sequence of basic anomalies and a position requirement specifying the relative position of each basic anomaly to all others in the pattern;

comparing grouped spatial signals within the context of those stored patterns in rail volumes;

deriving from results of comparison a high level recognition of flaws and the locations of flaws in the rails, whereby flaws inconsistent with recognized context are one of eliminated and reclassified.

4. A method for examining railroad rails for flaws using ultrasonic investigation technique and for identifying flaws in the rail on a real-time basis, comprising the steps of repetitively and regularly injecting pulses of a plurality of ultrasonic beams into the rails from test wheels mounted to travel along the rails, and detecting within the test wheels acoustic echoes caused at rail discontinuities by the ultrasonic beams to produce electrical signals representative of the acoustic echoes;

determining from electrical signals travel times of the acoustic echoes to the place of injection into the rails of the beams which caused the acoustic echoes;

while said ultrasonic beams are repetitively and regularly injected into the rails, deriving from said travel times, angles of travel, beam pulse speeds, and beam spreads of the ultrasonic beams inside the rails, spatial signals representative of the locations of the discontinuities along the rails;

combining spatial signals located within slices of the rail to derive volume counts and orientations of the number of discontinuities encountered in rail volumes formed by combined slices;

determining a distance along which a said detected rail discontinuity does not occur; generating said volume count when said distance exceeds a predetermined threshold value; deriving, from said volume counts and orientations, the locations, size, and type of flaws in the rails;

comparing said types of flaws with expected contexts for said flaws in said elongate material to one of eliminate and reclassify those flaws inconsistent with recognized context; and indicating the location of said flaws while pulses of ultrasonic beams are repetitively and regularly injected.

5. A method for examining an elongate material for flaws using ultrasonic investigation techniques and for identifying flaws in the material on a real-time basis, comprising the steps of:

repetitively and regularly injecting pulses of a plurality of ultrasonic beams into the elongate material from test devices mounted to travel along the elongate material, and detecting within the test devices acoustic echoes caused at material discontinuities by the ultrasonic beams to produce electrical signals representative of the acoustic echoes;

determining travel times of the acoustic echoes to the place of injection into the elongate material of the ultrasonic beams which caused the acoustic echoes;

while said ultrasonic beams are repetitively and regularly injected into the elongate material, deriving from said travel times, angles of travel, beam pulse speeds, and beam spreads of the ultrasonic beams inside the material, spatial signals representative of the locations of the discontinuities along the elongate material;

combining spatial signals located within slices of the elongate material to identify and locate flaws in and along the elongate material, while said ultrasonic beams are repetitively and regularly activated, including the steps of storing information representative of normal patterns of known material discontinuities and manufactured contexts, comparing combined spatial signals with said stored information to detect and identify unknown discontinuities and one of eliminate and reclassify those discontinuities inconsistent with recognized context; and indicating the locations of said material discontinuities.

6. The method for examining an elongate material as set forth in claim 5 wherein said combining step further comprises:

determining depths inside the elongate material of a discontinuity and the ultrasonic beams which caused echoes therefrom;

grouping spatial signals related to said discontinuity; and deriving from said grouping a basic anomaly recognition of spatially-correlated flaw patterns.

7. The method as claimed in claim 6 wherein said combining step still further comprises the steps of:

storing a plurality of patterns which consist of a grammar requirement defining a sequence of basic anomalies and a position requirement specifying the relative position of each basic anomaly to all others in the pattern;

comparing grouped spatial signals with said stored patterns;

deriving from results of comparison a high level recognition of flaws and the locations of flaws in the rails.

8. A method for examining an elongate material for flaws using ultrasonic investigation technique and for identifying flaws in the elongate material on a real-time basis, comprising the steps of:

repetitively and regularly injecting pulses of a plurality of ultrasonic beams into the elongate material from test devices mounted to travel along the elongate material and detecting within the test devices acoustic echoes caused at elongate material discontinuities by the ultrasonic beams to produce electrical signals representative of the acoustic echoes;

determining from electrical signals travel times of the acoustic echoes to the place of injection into the elongate material of the beams which caused the acoustic echoes;

while said ultrasonic beams are repetitively and regularly injected into the elongate material, deriving from said travel times angles of travel, beam pulse speeds, and beam spreads of the ultrasonic beams inside the material, spatial signals representative of the locations of the discontinuities along the elongate material;

combining spatial signals located within slices of the elongate material to derive volume counts and orientations of the number of discontinuities encountered in elongate material volumes formed by combined slices;

determining a distance along which a said detected elongate material discontinuity does not occur;

generating said volume count when said distance exceeds a predetermined threshold value; deriving, from said volume counts and orientations, the locations, size, and type of flaws in the elongate material;

comparing said types of flaws with expected contexts for said flaws in said elongate material to one of eliminate and reclassify types of flaws inconsistent with recognized context; and indicating the location of said flaws while pulses of ultrasonic beams are repetitively and regularly injected.

\* \* \* \* \*